United States Patent [19]

Schehlmann et al.

[11] Patent Number: 5,739,122

[45] Date of Patent: Apr. 14, 1998

[54] DEXTRAN ESTERS, THE PREPARATION THEREOF AND THE USE THEREOF FOR COATING OR EMBEDDING DRUGS

[75] Inventors: Volker Schehlmann, Mannheim; Kurt Heinz Bauer; Jan-Frederic Kesselhut, both of Freiburg, all of Germany

[73] Assignee: BASF Aktiengesellschaft, Ludwigshafen, Germany

[21] Appl. No.: 612,975

[22] PCT Filed: Sep. 7, 1994

[86] PCT No.: PCT/EP94/02988

§ 371 Date: Mar. 11, 1996

§ 102(e) Date: Mar. 11, 1996

[87] PCT Pub. No.: WO95/07936

PCT Pub. Date: Mar. 23, 1995

[30] Foreign Application Priority Data

Sep. 17, 1993 [DE] Germany ............... 43 31 539.9

[51] Int. Cl.$^6$ .................... A61K 31/72; C08B 37/02
[52] U.S. Cl. .................... 514/59; 514/964; 536/112
[58] Field of Search .................... 514/59, 964; 536/112

[56] References Cited

U.S. PATENT DOCUMENTS 4,411,891 10/1983 Mizutani et al. .................... 514/59
5,247,072 9/1993 Ning et al. .................... 536/97
5,484,776 1/1996 Racz et al. .................... 514/54

FOREIGN PATENT DOCUMENTS 41 36 324 5/1993 Germany.

OTHER PUBLICATIONS

Kurthals et al., *Acta Pham. Nord.*, vol. 1(4): 201–210 Abstract Only.
Larsen et al., *Acta Pharm. Nord.*, vol. 1(2): 57–66 Abstract Only.
Schacht et al., *Polym. Prepr. (ACS, Div. Polym. Chem.)*, vol. 31(2): 717–718, (1990) Abstract Only.
Larsen et al., *Pharm Res.*, vol. 6(12): 995–999, (1989) Abstract Only.
Larsen et al., *Int. J. Pharm.*, vol. 51(3): 233–240, (1989) Abstract Only.

*Primary Examiner*—John Kight
*Assistant Examiner*—Howard C. Lee
*Attorney, Agent, or Firm*—Keil & Weinkauf

[57] ABSTRACT

Dextran esters with a molecular weight of 10,000–10,000,000 and ester side chains which are derived from acids with 6–18 carbon atoms, where the degree of esterification is adjusted, depending on the number of carbon atoms in the side chains and the molecular weight, to a value of 0.04–1.1 so that the dextran esters are insoluble in water at room temperature and are broken down by colonic bacteria, and their use for coating and/or embedding pharmaceutical active ingredients or drug formulations.

7 Claims, No Drawings

DEXTRAN ESTERS, THE PREPARATION THEREOF AND THE USE THEREOF FOR COATING OR EMBEDDING DRUGS

The present invention relates to water-insoluble dextran esters, to a process for preparing them, to their use for coating and/or embedding pharmaceutical active ingredients or drug formulations, and to drugs containing an active ingredient coated by or embedded in a dextran ester.

Ancillary substances are becoming increasingly important in the development and formulation of modern drugs. Thus, it is not just a medicinal substance alone which is responsible for a specific effect but, on the contrary, the interplay with one or more added ancillary substances. Ancillary substances have particular importance for the timing and the site-specificity of release of the medicinal substance, as well as for absorption. On administration as oral drug forms to date the timing or site-specificity of release of the medicinal substance has been confined to the stomach and various regions of the small intestine by the choice of suitable coating materials. However, to date there are no suitable coating materials making it possible for the drug form to be transported unchanged and completely active as far as the colon in order to release the medicinal substance specifically there. A drug form of this type would be desirable, for example, for the local therapy of inflammatory disorders of the colonic mucosa such as Crohn's disease. In addition, it might be possible to describe new ways of treatment with peptide medicinal substances which, on oral administration, are digested by physiological or enzymatic effects of the gastric and small intestinal fluids and thus become inactive. The development of an oral peptide drug form will result in the advantage compared with other possible routes of administration, such as nasal, transdermal or pulmonary administration, that no other aids (eg. plasters, atomizers) are necessary. This leads to reduced costs of therapy and to increased compliance because the patient regards oral administration of medicinal substances as more natural and, moreover, can carry it out himself.

For specific release of medicinal substances in the human colon, the coating material must comply with a number of requirements:

1. The embedding or coating material must be insoluble in water and must be cleaved by bacterial enzymes in the colon.
2. It should swell in water just enough as is necessary for enzymatic attack.
3. It must be resistant to gastric fluids and small intestinal fluid.
4. The material and its breakdown products must be non-toxic and physiologically tolerated.

There is a marked difference in the density of bacterial colonization between the small intestine ($10^4$ organisms/ml) and the colon ($10^{14}$ organisms/ml). It is therefore possible to utilize the enzymatic activity of some bacteria in the colonic flora for cleaving a film coating which is stable in the small intestine.

J. Chem. Soc. 74 (1952) 5016 discloses stearyldextrans. However, no information about the molecular weight or the degree of substitution (degree of esterification) is to be found therein. Accordingly, there is also no disclosure of how these parameters must be set for the substances to be broken down by colonic bacteria.

DE 40 06 521 A1 (and the corresponding European Patent Application 450 176 A1) describes sugar-containing polymers for coating and embedding the medicinal substances. These sugar-containing polymers are used for coating and/or embedding pharmaceutical active ingredients which can be administered orally, and have the effect that the active ingredients contained in the polymers are released only when the colon is reached. The polymers described in this publication have the disadvantage that they require complicated preparation and are crosslinked with polyisocyanates.

DE 41 36 324 A1 discloses dextran derivatives which have a molecular weight of up to 20,000 and are intended as absorbents for bile acids.

DE 41 31 292 A1 discloses galactomannan derivatives for coating or embedding drugs, the galactomannans being etherified or esterified. The preparation process and the purification of the etherified or esterified galactomannan derivatives is, however, complicated and elaborate.

It is an object of the present invention to provide ancillary substances for drugs which comply with the abovementioned requirements for materials which can be broken down in the colon, are derived from easily obtainable starting materials and can be prepared and processed industrially without difficulties.

We have found that this object is achieved by dextran esters with a molecular weight of 40,000–10,000,000 and ester side chains which are derived from acids with 6–18 carbon atoms, where the degree of esterification is adjusted, depending on the number of carbon atoms in the side chains and the molecular weight, to a value of 0.04–1.1 so that the dextran ester is insoluble in water at room temperature and is broken down by colonic bacteria.

It has emerged, surprisingly, that it is possible to prepare, starting from dextrans, embedding materials which comply with the abovementioned requirements. A particular advantage emerges when the dextran esters according to the invention additionally have film-forming properties because, in this case, they are suitable not only as embedding materials but also as coating materials.

It is of particular importance in this connection that the dextran esters according to the invention are soluble or at least dispersible in environmentally compatible solvent mixtures such as water/alcohol mixtures because this increases the possibilities of applying the dextran esters as films.

The invention accordingly also relates to the use of the dextran esters for coating and/or embedding pharmaceutical active ingredients or drug formulations and to drugs which contains an active ingredient which acts in the colon or an active ingredient which is broken down on passing through the stomach or small intestine, coated with or embedded in a dextran ester according to the invention.

For the dextran esters according to the invention to be suitable as coating materials it is necessary for various factors to be taken into account.

Thus, the molecular mass and the degree of substitution are factors operating in opposite directions for the film formation on the one hand and for the degradability on the other hand. Choice of a high molecular weight favors film formation but the disintegration of the film after enzymatic attack is slowed down. If a high degree of substitution is achieved by synthesis, the stability of the films in water is improved but the swelling and the degradability are diminished.

The invention also relates to a process for preparing the dextran esters, which comprises dissolving dextran in a solvent composed of formamide and/or dimethyl sulfoxide, to which it is possible to add an amount of an aprotic polar organic solvent such that the dextran is still soluble, and adding a halide, particularly a chloride, of an acid with 6–18 carbon atoms in the presence of a proton scavenger in such a way that the temperature of the reaction mixture does not exceed 40° C. Employed as proton scavengers are amines, in particular pyridine.

The dextrans employed for preparing the dextran esters according to the invention can be obtained without difficulty.

They are obtained, for example, from cultures of species of Leuconostoc bacteria. The structure of the dextrans which can be isolated varies depending on the Leuconostoc species. Examples of dextrans which can be employed are described in the literature (J. Am. Chem. Soc. 76 (1964) 5041). The proportion of α-1.6 linkages in the dextrans, and thus in the resulting dextran esters, should, however, not be below 60%, because dextrans with a proportion of α-1.6 linkages below 60% can be broken down enzymatically by dextranase only under certain conditions. The degradability of dextrans by intestinal bacteria is moreover known (J. of Bact. 63 (1951) 424).

An example of a commercially available dextran is the type NRRL-512. This is isolated from cultures of Leuconostoc mesenteroides. Dextran NRRL-512 is an α-1,6-polyglucan. The proportion of α-1.6 linkages is about 96%. The remaining linkages are α-1,2 and α-1,3 linkages of the glucose monomers, which lead to branches with a chain length of one glucose unit. Dextran NRRL-512 is thus a virtually unbranched sugar polymer.

Dextrans can be obtained in many molecular weight ranges from 800 to 10,000,000. After the high molecular weight dextran has been isolated from the bacterial culture the latter is subjected to acid hydrolysis, and the various molecular weight ranges are obtained by fractionation with ethanol/water mixtures of different concentrations.

The molecular weight of the initial dextrans for the dextran esters according to the invention are chosen so that, after derivatization, products with the required breakdown and solubility or swelling properties can be obtained.

Dextran complies with some of the requirements mentioned at the outset which must be met by a coating which can be broken down in the colon. It is, however, soluble in water and must therefore be specifically rendered hydrophobic by substitution with suitable substituents. The nature and number of the substituents introduced are crucially determined by the solubility or swelling properties as well as the film formation and enzymatic degradability.

We have found that unsubstituted regions must be present in the dextran ester for enzymatic attack in the colon. However, the dextran esters according to the invention are not attacked by amylases which occur in the stomach and small intestine and are therefore stable in the small intestine.

Preferred dextran esters have ester side chains derived from acids with 8–16, in particular 8–12, carbon atoms, have a molecular weight of 40,000–1,000,000, in particular 60,000–400,000, and have a degree of esterification of 0.08–0.8, in particular 0.1–0.5.

The following dextran esters are particularly preferred in this connection:

Advisable for films and embeddings which can be broken down in the colon are dextran esters with lauryl substituents and degree of substitution (DS, degree of esterification) of 0.1–0.5, but preferably 0.1–0.2. The molecular weight of the lauryldextrans should be 150,000–1,000,000, but preferably 200,000–300,000.

By contrast, caproyldextrans with a DS of 0.1–0.5, but preferably 0.1–0.2, and a molecular weight of 1,000,000–10,000,000 are suitable only for embeddings; as are stearyldextrans with a DS of 0.1–0.5, but preferably 0.1–0.2, and a molecular weight of 150,000–1,000,000, but preferably 200,000–300,000; furthermore lauryldextrans with a DS of 0.2–0.5 and a molecular weight of 60,000–150,000.

The dextran esters according to the invention can be prepared as follows, for example:

Dextran is dried in a vacuum drying oven and dissolved in a mixture of formamide and pyridine in a round-bottomed flask with calcium chloride drying tube. Subsequently the fatty acid chloride is added and the reaction mixture is stirred at room temperature for four hours. The resulting product is precipitated in water, separated off and washed several times with water. The product is finally washed several times with a mixture of ethyl acetate and ethanol and dried.

J. Am. Soc. 74 (1952) 5339 discloses a comparable process for preparing dextran triacetates.

The esters according to the invention must be prepared under anhydrous conditions. Solvents suitable for this are in particular aprotic organic polar solvents such as formamide, N-methylpyrrolidone, dimethylformamide, dimethylacetamide and/or dimethyl sulfoxide. The esterification can also be carried out without solvent in the melt. In this case, the solvent for the polymer is the acylating reagent or the reactant, for example alkaloyl halide, alkaloyl anhydride or chloroacetic anhydride. The esterification takes place, for example, at from 0° to 160° C., or at the boiling point of the solvent, by reacting the appropriate dextrans with $C_6$–$C_{18}$-alkanoyl halides, preferably $C_8$–$C_{16}$-alkanoyl halides or $C_6$–$C_{18}$-alkanoyl anhydrides, preferably $C_8$–$C_{16}$-alkanoyl anhydrides.

This acylation expediently takes place in the presence of basic compounds such as pyridine.

The basic substances should be present in excess relative to the initial alkanoyl compound, for example in an excess of 0.1–0.2 mole per mole of initial alkanoyl component.

The invention particularly relates to use of the dextran esters according to the invention for producing film coatings and embeddings of pharmaceutical active ingredients and in particular active ingredients which can be administered orally, or pharmaceutical formulations which can be administered orally and release the active ingredient in the colon. This is achieved by the active ingredients or formulations with active ingredients, for example granules, pellets or tablets, being coated with and/or embedded in the dextran esters according to the invention.

The coating of the active ingredients or of the pharmaceutical formulations, that is of the formulations in which the active ingredients are incorporated together with conventional or necessary pharmaceutical ancillary substances, takes place by methods known in pharmaceutical technology or the conventional processes for coating drug forms. The embedding of therapeutically active ingredients likewise takes place by methods known in pharmaceutical technology. It is furthermore possible also to use conventional pharmaceutical ancillary substances or additives in this case, for example plasticizers (especially for coatings), flavorings, sweeteners, ancillary substances such as talc, calcium carbonate, mannitol, cellulose powder, soluble colorants and pigments.

Additional ancillary substances which can be employed, their use and the production of drug formulations have been described many times, eg. in DE 41 31 292 A1, columns 5 to 10, and are therefore known to the skilled worker.

Examples of suitable active ingredients which can preferably be formulated with the dextrans according to the invention are those pharmaceutical active ingredients which are broken down or digested in the stomach or small intestine and therefore have not been amenable to oral administration in the past, and drugs which are intended to act only after reaching the colon, such as drugs acting on disorders of the colon, and peptide drugs. Examples are: peptides, cardiovascular therapeutic agents, antirheumatics/ analgesics, compositions for the therapy of disorders of the colon such as Crohn's disease and ulcerative colitis, antiasthmatics, antifibrinolytics, antihemorrhagics, antitumor compositions, enzyme products, antibiotics, antimycotics, and substances acting on the central nervous system.

Examples of peptide active ingredients are: ACTH (adrenocorticotropic hormone), corticostatin, calcitonin, insulin, oxytocin, somatostatin and analogs, LHRH analogs, bombesin analogs, cholecystokinin and derivatives, endothelin and analogs, thrombin inhibitors, peptide growth factors (eg. IGF, EGF, NGF), magainins (PGS peptides), gastrin analogs, bradykinin analogs, parathyroid hormone analogs, neurokinin and analogs, VIP and analogs, ANP (atrial natriuretic peptide) and analogs, neokyotrophin and analogs, angiotensin analogs, encephalins, dynorphins, dermorphins, deltorphins, renin-inhibiting peptides, tumor growth factor peptides, MSH (melanocyte stimulating hormone) analogs, mitotoxins, tyrphostins, chromogranin A, thymopentin, TRH and analogs, substance P, tuftsin, fibronectin, and peptide immunomodulators such as cyclosporin A, FK 506, neuropeptide Y and NPK.

Peptides prepared biotechnologically, especially lower peptides, are preferably used according to the invention.

EXAMPLES

1. Caproyldextrans

1.1 Preparation

Dextrans with molecular weights of 200,000–300,000 and 1,000,000–10,000,000 were employed for the synthesis. The reaction medium used was pyridine (inhomogeneous swelling synthesis) or formamide (homogeneous reaction mixture). The acid chlorides were used as acylating reagents.

The specific procedure was as follows:

Caproyldextran with DS=0.13 (DS=degree of esterification)

4.0 g of dextran (molecular weight 1,000,000–10,000,000) are suspended in 144 g of pyridine in a 250 ml round-bottomed flask with jacketed coil condenser and drying tube. The mixture is stirred at 70° C. for two hours, 2.1 g of caproyl chloride are added, and the mixture is stirred for a further three hours. The precipitated product is washed several times with water and acetone.

The caproyldextran with DS=0.08 was prepared in a similar way.

Caproyldextran with DS=1.7

4.0 g of dextran are suspended in 136 g of pyridine in a 250 ml round-bottomed flask with jacketed coil condenser and drying tube. The mixture is stirred at 70° C. for two hours, 10.0 g of caproyl chloride are added, and the mixture is stirred for a further three hours. The precipitated product is washed several times with water and acetone.

The caproyldextran with DS=0.62 was prepared in a similar way.

1.2 Characterization of the products

1.2.1 Determination of the degree of substitution

The esterified caproyl radicals were determined quantitatively by gas chromatography as methyl caproate after alkaline hydrolysis. After computation of the peak areas, the degree of substitution DS is obtained from the following formula I $$DS = \frac{Mol_{Cap} \times 162.14}{(Mass_{Po} - MW_{Cap} \times Mol_{Cap}) \cdot \left(1 + \frac{Mol_{Cap}}{MW_{Cap} \times Mol_{Cap}} \times MW_H \right)} \quad \text{I}$$

Where the parameters have the following meanings:

$Mol_{Cap}$ = mol of caproyl substituent $Mass_{Po}$ = weight of polymer $MW_{Cap}$ = molecular weight of the caproyl substituent $MW_H$ = molecular weight of a hydrogen atom

1.2.2 Solubility

The caproic esters which are insoluble in water and were obtained from dextran of molecular weight 1,000,000–10,000,000 are soluble only in formamide and DMSO.

The products obtained when a lower molecular weight is chosen are soluble in various polar solvents depending on the degree of substitution.

| | Solubility of caproyldextrans | | | |
|---|---|---|---|---|
| Mol. weight | Degree of substitution | Methanol | Acetone | Formamide |
| 1,000,000–10,000,000 | 0.08 | | | X |
| 1,000,000–10,000,000 | 0.13 | | | X |
| 200,000–300,000 | 0.62 | X | | |
| 200,000–300,000 | 1.7 | | X | |

1.2.3 Film formation

The caproyldextrans obtained from dextran of molecular weight 200,000–300,000 form stable films from the stated solvents. It was not possible to form films from the products of higher molecular weight.

| | Formation and stability of caproyldextran films | | | |
|---|---|---|---|---|
| Mol. weight | Degree of substitution | Film formation from org. solvent | Film formation from aq. suspension | Stability of the films in water |
| 1,000,000–10,000,000 | 0.08 | no | poor | — |
| 1,000,000–10,000,000 | 0.13 | no | poor | — |
| 200,000–300,000 | 0.62 | yes | no | o |
| 200,000–300,000 | 1.7 | yes | no | + |

Where the symbol—in the "stability" column means disintegration of the film in water, a symbol o means a loss of weight of the film with swelling above 1%, and a + symbol means a loss of weight of the film below 1%.

1.2.4 Uptake of water by the caproyldextran films

It is necessary for an enzymatic attack that the films take up water to a limited extent because the enzymes of the colonic flora are dissolved in the aqueous medium. During the uptake of water by the films, the enzymes reach the linkages in the polymer which are to be cleaved.

The uptake of water is determined by the following formula.

$$A = \frac{G_t - G_0}{G_0} \times 100$$

where A is the weight gain in percent, $G_o$ is the weight of the dry film and $G_t$ is the weight of the swollen film saturated with water.

The following values were found:

| Degree of substitution | 1.7 | 0.62 |
|---|---|---|
| Water uptake (%) | 3.3 | 37.5 |

1.2.5 Degradability with pure dextranase

The degradability of the caproyldextrans was examined by thin-layer chromatography. The low molecular weight substances were not attacked by the enzyme because the degree of substitution required in this case to obtain water-insoluble products is also to high.

With the higher molecular weight caproic esters, water-insoluble products are obtained even with a low degree of substitution above DS=0.1. The degradability is retained at this low degree of substitution.

1.3 Summarizing assessment of the caproyldextrans

The magnitudes of the molecular weights were initially chosen to be just sufficient for it to be possible, after substitution has taken place, to form adequately stable films in the dry and swollen state. This requirement was met by introducing the $C_6$ substituent when the molecular weight of the initial dextrans was 200,000–300,000. A degree of substitution above 0.6 at this molecular weight leads to water-insoluble derivatives. However, enzymatic attack is no longer possible at this degree of substitution.

Choice of a higher molecular weight of the initial dextran for the synthesis, in the range from 1,000,000 to 10,000,000, results in water-insoluble products even with a degree of substitution above 0.1. Enzymatic degradability is still guaranteed in this case. It is not possible to form films from organic solvents with these high molecular weight derivatives because of their low solubility. Although thermogelation from aqueous suspension led to films, these did not have adequate stability in water. The caproyldextrans with the higher molecular weights are therefore suitable as embedding materials for administration in the colon.

Characterization of caproyldextrans in respect of their suitability as coating degradable in the colon.

| Mol. weight | Degree of substitution | Soluble in | Film formation possible from solvent/ $H_2O$ | Swelling of the film in water | Degradability by dextranase | Suitability as coating degradable in the colon |
|---|---|---|---|---|---|---|
| 1 × 10⁶– 10 × 10⁶ | 0.08 | Formamide DMSO | no/no | — | yes | as embedding |
| 1 × 10⁶– 10 × 10⁶ | 0.13 | Formamide DMSO | no/poor | disintegrates | yes | as embedding |
| 200 × 10³– 300 × 10³ | 0.62 | Methanol | yes/no | 37.5% | no | no |
| 200 × 10³– 300 × 10³ | 1.7 | Acetone | yes/no | 3.3 | no | no |

2. Stearyldextrans 2.1 Preparation

A dextran with a molecular weight of 200,000–300,000 was employed.

A process for preparing stearyldextrans is described in the literature (J. Chem. Soc. 74 (1952) 5016). This makes use of what is called the actuator method with chloroacetic anhydride and sodium perchlorate as catalyst. During the synthesis, the anhydride corresponding to stearic acid is formed from it by reaction with the actuator. This anhydride then preferentially reacts with the hydroxyl groups of the dextran. No chloroacetyl groups are detectable in the reaction products. An excess of chloroacetic anhydride is used as solvent. The reaction is carried out at 80° C. and is inhomogeneous. It was possible to obtain stearyldextrans with variable degrees of substitution by adding different amounts of stearic acid.

The specific procedure was as follows:

Stearyldextran with DS=0.32

2.0 g of dextran, 4.0 g of stearic acid, 20.0 g of chloroacetic anhydride and 50 mg of sodium perchlorate are weighed into a 50 ml round-bottomed flask with jacketed coil condenser and heated to 80° C. with stirring. The reaction is stopped after 8 hours and the precipitated product is washed several times with water and acetone.

The stearyldextran with DS=0.48 was prepared in a similar way.

Stearyldextran with DS=1.16

2.0 g of dextran are suspended in 140 g of pyridine in a 250 ml round-bottomed flask with jacketed coil condenser and drying tube and stirred at 70° C. for 2 hours. 8.0 g of stearoyl chloride are added, and the mixture is stirred for a further 4 hours. The precipitated product is washed several times with water and acetone.

2.2 Characterization of the products 2.2.1 Determination of the degree of substitution The stearyl substituents are eliminated by alkaline hydrolysis, isolated and determined quantitatively by gas chromatography as methyl stearate after esterification with methanol. Methyl heptadecanoate is used as internal standard for the evaluation.

The degree of substitution was calculated from formula I as for caproyldextran.

2.2.2 Solubility

The resulting stearyl derivatives are soluble only in DMSO and formamide. A highly substituted lipophilic stearyldextran with DS=1.16 showed serious swelling in dichloromethane. However, all the products were insoluble in solvents suitable for film coating tablet cores (eg. isopropanol).

| Solubility of stearyldextrans | | | |
|---|---|---|---|
| Degree of substitution | Formamide | DMSO | Dichloromethane |
| 0.32 | X | X | |
| 0.48 | X | X | |
| 1.16 | X | X | Swelling |

2.2.3 Film formation

Only very poor films can be formed from the stearyldextrans obtained. The more highly substituted derivative showed a tendency to film formation from dichloromethane.

Formation and ability of stearyldextran films

| Degree of substitution | Film formation from org. solvent | Film formation from aq. suspension | Stability of the films in water |
|---|---|---|---|
| 0.32 | no | no | |
| 0.48 | no | no | |
| 1.16 | poor | no | o |

2.2.4 Uptake of water by the stearyldextran film

The resulting film was investigated in the same way as the caproyldextran films.

A water uptake of 3.75% was found with a degree of substitution of 1.16.

2.2.5 Degradability with pure dextranase

The degradability was examined by thin-layer chromatography. The two less substituted products are attacked by the enzyme. The stearyldextran with DS=1.16 is not broken down.

2.3 Summarizing assessment of the stearyldextrans

It is possible to obtain water-insoluble products whose enzymatic degradability is retained with the lipophilic stearic acid substituents and with a chosen molecular weight of 200.000–300.000 and a degree of substitution below 0.5. Films cannot be obtained from these products because of their poor solubility properties. However, they are suitable as embedding materials for specific administration in the colon. Although the highly substituted stearyl derivative has a tendency to form films it is not broken down.

Characterization of stearyldextrans in respect of their suitability as coating degradable in the colon

| Degree of substitution | Soluble in | Film formation possible from solvent/H$_2$O | Swelling of the films in water | Degradability by dextranase | Suitability as coating degradable in the colon |
|---|---|---|---|---|---|
| 0.32 | Formamide DMSO | no/no | — | yes | as embedding |
| 0.48 | Formamide DMSO | no/no | — | yes | as embedding |
| 1.16 | Swelling in dichloromethane | yes/no | 3.75 | no | no |

3. Lauryldextrans

3.1 Preparation

Dextrans with molecular weights in the ranges 200.000–300.000, 120.000–170.000 and 60.000–90.000 were employed.

The synthesis is carried out in formamide, in which dextran is very soluble. Since formamide tends to decompose at elevated temperature, especially under the influence of water-attracting agents, the synthesis is carried out at room temperature. Pyridine was employed as proton scavenger. The appropriate acid chloride is used as acylating agent. Lauryl chloride forms a type of gel complex with formamide, and this may lead to considerable problems with viscosity during the synthesis. These can be eliminated by adding excess solvent. The use of pyridine as proton scavenger proved to be more favorable than other bases which are solid at room temperature, such as 4-dimethylaminopyridine, for reducing the viscosity of the reaction mixture.

4-Dimethylaminopyridine was employed as base catalyst besides pyridine. This had the advantage that it was easier to remove on purification of the reaction product than was pyridine. Because of the possibility of decomposition of the formamide under the influence of the acid chloride, the synthesis is carried out at room temperature. In order to have reaction times as short as three to four hours with the comparatively unreactive lauryl chloride, the acylating agent was added in large excess. This makes the reaction mixture cloudy, but has no effect on the reproducibility of the synthesis. It may therefore be assumed that dextran and resulting dextran esters remain in solution during the synthesis and merely part of the acylating agent remains undissolved. The mixture remains homogeneous on addition of smaller amounts of acid chloride.

The specific procedure was as follows:

Lauryldextran with DS=0.08

3.0 g of dextran and 2.2 g of 4-dimethylaminopyridine are dissolved in 85 g of formamide in a 250 ml round-bottomed flask with condenser and drying tube, and 9.6 g of lauryl chloride are added. The mixture is stirred at room temperature for 3.5 hours, and the reaction is stopped by adding water. The precipitated product is washed several times with a mixture of ethanol and ethyl acetate in the ratio 80:20.

Lauryldextran with DS=0.11

6.0 g of dextran are dissolved in 90.0 g of formamide in a 250 ml round-bottomed flask with condenser and drying tube, and 60.0 g of pyridine and 8.0 g of lauryl chloride are added. The mixture is stirred at room temperature for 3.5 hours, and the reaction is stopped by adding water. The precipitated product is washed several times with a mixture of ethanol and ethyl acetate in the ratio 80:20. It is then washed several times with water.

Lauryldextran with DS=0.19

3.0 g of dextran and 2.2 g of 4-dimethylaminopyridine are dissolved in 81 g of formamide in a 250 ml round-bottomed flask with condenser and drying tube, and 14.1 g of lauryl chloride are added. The mixture is stirred at room temperature for 3.5 hours, and the reaction is stopped by adding water. The precipitated product is washed several times with a mixture of ethanol and ethyl acetate in the ratio 80:20. It is then washed several times with water.

The other lauryldextrans were each prepared in a similar way.

3.2 Characterization of the products

3.2.1 Determination of the degree of substitution

The substituents were determined quantitatively by gas chromatography as methyl laurate after elimination, isolation and esterification with methanol. Methyl myristate is used as internal standard.

The degree of substitution DS was calculated from formula I as for caproyldextran.

3.2.2 Solubility

For a molecular weight of the initial dextrans of 200.000–300.000, the degree of substitution must be above 0.06 in order to obtain water-insoluble derivatives. If a smaller molecular weight is employed, a somewhat higher degree of substitution is necessary to obtain products of similar solubility.

Lauryldextrans with degrees of substitution above these limits form colloidal solutions in binary solvent mixtures, it always being necessary to add water to the organic component (isopropanol/ethanol). The opalescence disappears on raising the temperature. The clear point is from 40° C. to 60° C. depending on the degree of substitution and nature of the organic component used. This is important for a possible thermal instability of active ingredients or ancillary substances on application of the films to tablet cores from warm solutions.

| Solubility of lauryldextrans | | | | |
|---|---|---|---|---|
| 60,000–90,000 | 0.12 | X | | |
| 60,000–90,000 | 0.30 | | X | |
| 120,000–170,000 | 0.08 | X | | |
| 120,000–170,000 | 0.19 | | X | 40° C. |
| 120,000–170,000 | 0.28 | | X | |
| 200,000–300,000 | 0.06 | X | | |
| 200,000–300,000 | 0.11 | | X | 55° C. |
| 200,000–300,000 | 0.24 | | X | |

3.2.3 Film formation

A tendency to film formation is shown at a molecular weight above 120,000. Films of good quality are obtained with derivatives with a molecular weight above 200,000. It was possible to obtain the films both from cold or hot solutions and from aqueous suspensions at 37° C. In order to obtain homogeneous films by thermogelation, the particle size in the suspension when obtaining the film should be below 30 μm in the swollen state.

The films obtained from derivatives with a molecular weight of 120,000–170,000 disintegrate in water within 30–120 minutes although these products are water-insoluble derivatives.

| | | Formation of lauryldextran films | | |
|---|---|---|---|---|
| Mol. weight | Degree of substitution | Film formation from org. solvent | Film formation from aq. suspension | Stability of the films in water |
| 60,000–90,000 | 0.30 | no | no | — |
| 120,000–170,000 | 0.19 | yes | yeS | disintegration after 30 min |
| 120,000–170,000 | 0.28 | yes | ye | disintegration after 100 min |
| 200,000–300,000 | 0.11 | yes | yes | + |
| 200,000–300,000 | 0.24 | yes | yes | + |

3.2.4 Uptake of water by the films

The uptake of water was determined by the method described.

The following values were found:

| Degree of substitution: | 0.28* | 0.11** | 0.24** |
|---|---|---|---|
| Water uptake: | 198 | 230 | 178 |

*Dextran 150
**Dextran 250

3.2.5 Degradability with pure dextranase

All the resulting products are enzymatically degradable. After the enzymatic attack is complete, a water-insoluble residue remains with some water-insoluble products depending on the degree of substitution. Lauryldextran with DS=0.11 is cleaved to completely water-soluble breakdown products. The solubility limit in water is at a molecular weight of about 60,000.

3.3 Summarizing assessment of the lauryldextrans

Substitution with lauric acid makes it possible to obtain dextran derivatives which comply in all respects with the requirements for a film-forming coating degradable in the colon. Insolubility in water results at a molecular weight of the dextran employed of 60,000–90,000 above DS=0.12, of 120,000–170,000 above DS=0.08 and of 200,000–300,000 above DS=0.06. For the films to be stable in water it is necessary for the degree of substitution to be 0.1–0.2 at a molecular weight of 200,000–300,000 which is required for film formation. The products form colloidal solutions in 50% ethanol and 50% isopropanol. Raising the temperature results in clear polymer solutions. Films can be obtained from such solutions. Thermogelation from aqueous suspension is likewise possible. For lauryldextran films with adequate stability in water to be formed it is necessary for the molecular weight of the initial dextrans to be above 200,000.

It has thus been possible to prepare two substances which are particularly suitable. However, the derivative with DS=0.11 additionally has better breakdown properties than that with DS=0.24 because completely water-soluble breakdown products are produced. Release of a medicinal substance is thus ensured on the one hand by the diminution in the mechanical strength of the films, and on the other hand owing to dissolution of the film.

| Charcterization of the lauryldextrans in respect of suitability as coatings degradable in the colon | | | | | | |
|---|---|---|---|---|---|---|
| Mol. weight | Degree of substitution | Soluble in | Film formation possible from solvent/ $H_2O$ | Uptake of water by the films | Breakdown by dextranase possible | Suitability as coating degradable in the colon |
| 120,000–170,000 | 0.28 | Isopropanol 50% | yes/yes | 198% | yes | possibly as embedding, film disintegrates |
| 200,000–300,000 | 0.11 | Isopropanol 50% | yes/yes | 230% | yes | yes |
| 200,000–300,000 | 0.24 | Isopropanol | yes/yes | 178% | yes | yes |

4. Comparative test with acetyldextrans

Some acetyldextrans were prepared as comparative substances. Dextrans with a molecular weight of 1,000,000–10,000,000 were employed.

Preparation took place as described in the literature (J. Am. Chem. Soc. 74 (1952) 5339).

The specific procedure was as follows, for example:

Acetyldextran with DS=3

3.0 g of dextran are dissolved in 122.6 g of formamide in a 250 ml round-bottomed flask with jacketed coil condenser and drying tube, and subsequently 10.5 g of pyridine and sufficient acetic anhydride for the molar ratio of reactive acetyl groups to free hydroxyl groups in the dextran to be 1.2:1 are added. The mixture is stirred at room temperature for three hours. The reaction is stopped by adding water. The reaction product is precipitated and washed several times with water. The other acetyldextrans were prepared in a similar way.

Characterization took place as described for the other dextran esters. Although film-forming compounds were obtainable it was found that below a degree of substitution of 1.2 acetyldextran is water-soluble and thus unsuitable for the purposes according to the invention. Water-insoluble acetyldextrans with DS>1.2 are not broken down and are therefore likewise unsuitable (see table below).

Characterization of acetyldextrans with different degrees of substitution in respect of suitability as coating degradable in the colon.

| Degree of substitution DS | Soluble in | Film formation possible from solvent/H$_2$O | Uptake of water by the films | break-down by dextranase possible | Suitability as coating degradable in the colon |
|---|---|---|---|---|---|
| 3 | Tetra-chlor-ethane | yes/no | 1.8% | no | no |
| 2.4 | Di-chloro-methane | yes/no | 9.5% | no | no |
| 1.84 | Acetone | yes/no | 58.2% | no | no |
| 1.4 | Methanol | yes/no | 135.5% | no | no |

5. Analytical methods 5.1 Determination of the degree of substitution of caproyldextran 50.0 mg of caproyldextran and 20.0 mg of methyl heptanoate are mixed with 5 ml of 10% KOH in a vial, which is then capped and kept at 90° C. for 3 hours. After cooling, the solution is transferred into a 50 ml separating funnel, acidified with concentrated HCl and extracted by shaking three times with 10 ml of diethyl ether each time. The ether phases are dried over sodium sulfate and transferred into a 50 ml round-bottomed flask, and the ether is stripped off in a rotary evaporator. The residue is mixed with 10.0 ml of methanol and 5.0 ml of 50% methanolic boron trifluoride solution and refluxed for 30 minutes. The reaction is stopped by adding 5 ml of water, and the cooled reaction mixture is extracted by shaking three times with 5 ml of hexane each time. The dried hexane phases are combined and used as solution for injection for the gas chromatography.

To determine the factor, 20.0 mg of each of methyl caproate and methyl heptanoate are dissolved in 5.0 ml of hexane and injected. The peak areas are evaluated and compared.

Gas chromatography:

Column: DEGS

Oven temperature: 70° C.

Injector temperature: 100° C.

Volume injected: 1 µl

The degrees of substitution of the other dextran esters were determined in a similar way (calculation with the above formula I).

5.2 Obtaining films 5.2.1 From organic solvents 100 mg of dextran ester are dissolved in 2 ml of a suitable solvent and poured into a Teflon dish with a diameter of 3 cm. The solvent is left to evaporate at 37° C.

5.2.2 Thermogelation 200 mg of dextran ester are suspended in 2 ml of water. After the polymer has swollen for half an hour, the suspension is dispersed with an Ultraturrax for 5 minutes. The suspension is poured into a Teflon dish with a diameter of 3 cm. The film is obtained by evaporating the water at 37° C.

5.3 Uptake of water by the films 10 mg of a homogeneous film are placed in 5 ml of water. After swelling is complete, water is removed from the surface face of the film using filter paper, and the film is re-weighed. The uptake of water is reported as a percentage.

5.4 Degradability of the dextran esters

Investigation of the degradability by thin-layer chromatography 50 mg of dextran ester are suspended in 5 ml of phosphate buffer pH 6.8. After one hour, 1 ml of a dextranase solution which contains 6 U/ml enzyme is added. The mixture is incubated at 37° C. for one hour, and the enzymatic reaction is stopped by adding 100 µl of methanol. The clear supernatant is applied to the plate. 50 mg of unsubstituted dextran is treated in the same way as blank.

Thin-layer chromatography:

Volume applied: 20 µl

Band width: 15 mm

Migration distance: 15 cm

Mobile phase: 1-propanol:butanol:nitromethane:water in the ratio 4:1:2:3

Comparisons: 0.1% strength solutions of glucose, isomaltose and isomaltotriose

Detection: Eckert's reagent/120° C.

In summary, it has been found that by varying the substituent, degree of substitution and molecular weight of the initial dextran, it was possible to prepare specifically derivatives which comply with all the requirements in respect of their suitability as coatings degradable in the colon. Molecular weights in the range 60,000–10,000,000 were employed. On substitution with $C_6$–$C_{12}$-fatty acids, the molecular weight of the dextran is preferably above 200,000 for it to be possible to obtain mechanically stable films in the dry and swollen state from the products. A tendency to film formation is evident even at a molecular weight of about 120,000. The stability of such films is, however, low, especially in the swollen state. It was possible to form only inadequate films from stearyldextrans. Relatively large unsubstituted regions must be present in the polymer for enzymatic attack to be possible. Below a preferred degree of substitution of 0.5 the degradability is in any event retained. Water-insoluble derivatives were therefore obtained with suitable substituents at this degree of substitution which has been found to be optimal. Introduction of lauryl substituents made it possible to obtain derivatives which comply with all the requirements. Stable films, in the dry and swollen state, are obtained at a molecular weight above 200,000 and a degree of substitution above 0.1. It is possible to obtain films from organic solvents, eg. 50% isopropanol, or by thermogelation at 37° C. Degradability of the product is ensured at this low degree of substitution.

We claim:

1. A dextran ester with a molecular weight of 60,000–400,000, ester side chains of 8–12 carbon atoms and a degree of esterification of 0.04–1.1, said dextran ester is insoluble in water at room temperature and is capable of being broken down by colonic bacteria.

2. Pharmaceutical active ingredients or drug formulations, coated with or embedded in a dextran ester with a molecular weight of 10,000–1,000,000, ester side chains of 6–18 carbon atoms and a degree of esterification of 0.04–1.1, said dextran ester is insoluble in water at room temperature and is capable of being broken down by colonic bacteria.

3. A drug composition which contains a pharmaceutically active ingredient, which acts in the colon or a pharmaceutically active ingredient, which is broken down on passing through the stomach or small intestine, coated with or embedded in a dextran ester of with a molecular weight of 10,000–1,000,000, ester side chains of 6–18 carbon atoms and a degree of esterification of 0.04–1.1, said dextran ester is insoluble in water at room temperature and is capable of being broken down by colonic bacteria.

4. The drug composition of claim 3, which contains a peptide as the pharmaceutically active ingredient.

5. The drug composition of claim 3, which is in the form of a tablet, granule or capsule.

6. The drug composition of claim 4, which is in the form of a tablet, granule or capsule.

7. The drug composition of claim 3, in which the dextran ester has a molecular weight of 60,000–400,000.

* * * * *